United States Patent
Hayes et al.

(10) Patent No.: US 6,881,745 B2
(45) Date of Patent: Apr. 19, 2005

(54) PHARMACEUTICAL COMPOSITIONS FOR POORLY SOLUBLE DRUGS

(75) Inventors: David Hayes, Rostrevor (AU); Angelo Mario Morella, Athelstone (AU)

(73) Assignee: F H Faulding & Co Limited, Melbourne (AU)

( * ) Notice: Subject to any disclaimer, the term of this patent is extended or adjusted under 35 U.S.C. 154(b) by 0 days.

(21) Appl. No.: 10/461,503

(22) Filed: Jun. 16, 2003

(65) Prior Publication Data

US 2003/0225104 A1 Dec. 4, 2003

Related U.S. Application Data

(62) Division of application No. 10/175,883, filed on Jun. 21, 2002, which is a continuation of application No. PCT/AU00/01592, filed on Dec. 22, 2000.

(30) Foreign Application Priority Data

Dec. 23, 1999 (AU) ............................................. PQ4854
May 12, 2000 (AU) ............................................. PQ7450

(51) Int. Cl.$^7$ ......................... A01N 43/64; A61K 31/41
(52) U.S. Cl. .................. 514/359; 514/255.06; 514/384; 424/408
(58) Field of Search ................................ 514/359, 384, 514/255.06, 772

(56) References Cited

U.S. PATENT DOCUMENTS

| | | | |
|---|---|---|---|
| 5,340,591 A | | 8/1994 | Nakano et al. |
| 5,633,015 A | * | 5/1997 | Gilis et al. .................. 424/490 |

FOREIGN PATENT DOCUMENTS

| | | |
|---|---|---|
| EP | 1027886 A2 | 8/2000 |
| WO | WO 98/00113 A1 | 1/1998 |
| WO | WO 00/40220 A1 | 7/2000 |

OTHER PUBLICATIONS

Kai et al., Chem. Pharm. Bull., vol. 44, No. 3, pp. 568–571 (1996).

* cited by examiner

*Primary Examiner*—Alton Pryor
(74) *Attorney, Agent, or Firm*—Birch, Stewart, Kolasch & Birch, LLP

(57) ABSTRACT

The present invention provides a pharmaceutical composition of a practically insoluble drug, wherein the composition may be administered with food or without food. The composition may be in the form of a solid dispersion of the practically insoluble drug and a polymer having acidic functional groups, and the composition may in vitro form a suspension.

16 Claims, 2 Drawing Sheets

PHARMACEUTICAL COMPOSITIONS FOR POORLY SOLUBLE DRUGS

Figure 1:
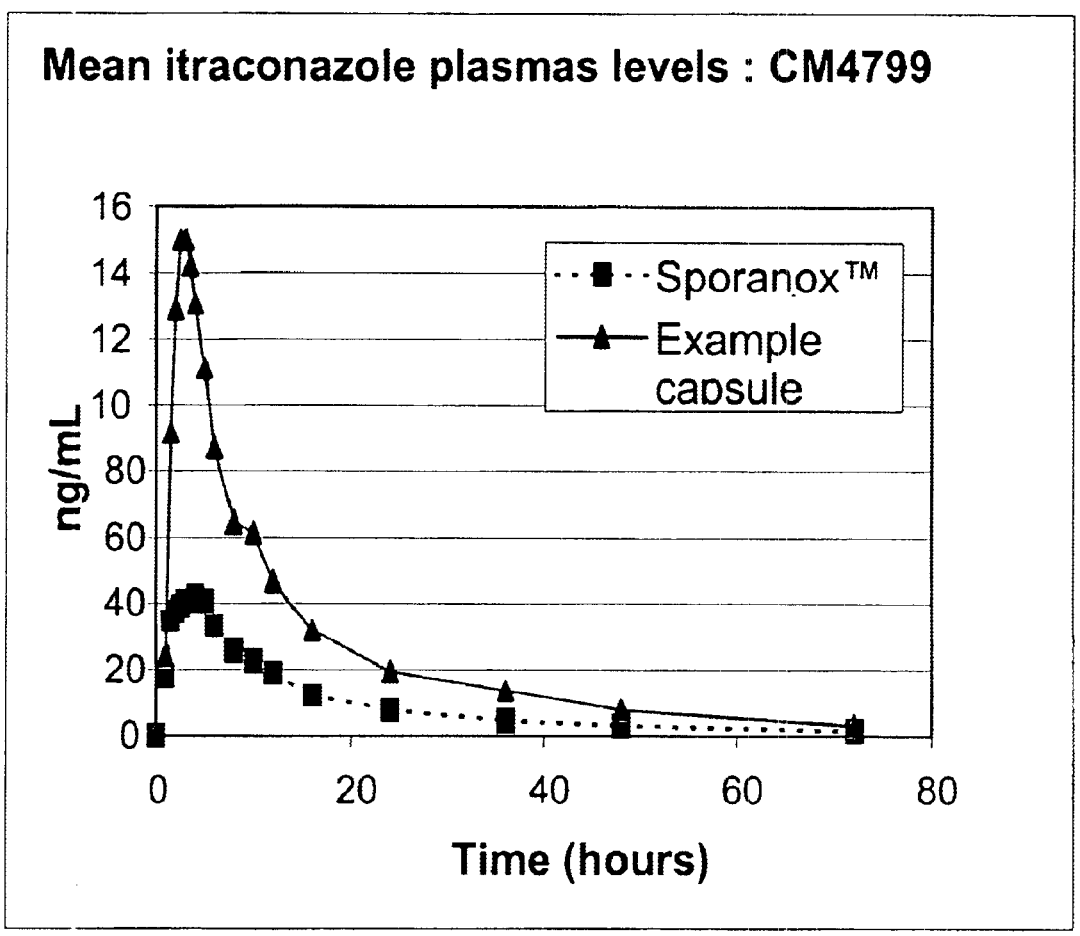

This application is a divisional of co-pending application Ser. No. 10/175,883, filed on Jun. 21, 2002 and for which priority is claimed under 35 U.S.C. §120. Application Ser. No. 10/175,883 is a Continuation of PCT International Application No. PCT/AU00/01592 filed on Dec. 22, 2000. The entire contents of each of the above-identified applications are hereby incorporated by reference. This application also claims priority of Application No. PQ4854 and PQ7450 filed in Australia on Dec. 23, 1999 and May 12, 2000, respectively under 35 U.S.C. §119.

FIELD OF THE INVENTION

The present invention relates to improved pharmaceutical compositions of drugs that are practically insoluble in aqueous media. The present invention also relates to a process for preparing the compositions. Furthermore, the present invention relates to improved dosage forms for the administration of the compositions.

BACKGROUND OF THE INVENTION

Drugs that are totally water-insoluble, or are at least poorly water-soluble, are usually characterised by low absorption and poor bioavailability, and present special difficulties when formulating dosage forms therefor. For the purposes of this specification, such drugs will be referred to as being "practically insoluble".

Indeed, it has been reported that the bioavailability of many practically insoluble drugs is limited by their dissolution rates and solubility, which in turn are understood to be controlled by the surface area that they present for dissolution. As such, attempts to improve the bioavailability of these practically insoluble drugs have often focussed on particle size reduction.

Examples of attempts to improve the bioavailability of such drugs are illustrated in international patent applications PCT/EP93/02327 and PCT/EP98/01773 both to Janssen Pharmaceutica N.V. These applications both relate to dosage forms of azole antifungals, such as itraconazole and saperconazole, which are said to be only very sparingly soluble in water, and both describe the incorporation of the drug with water-soluble polymers and the subsequent coating of the mixture on small beads. In PCT/EP93/02327 the beads are 600 to 700 micrometre in diameter, whereas in PCT/EP98/01773 the beads are 250 to 355 micrometre in diameter.

The dosage forms in both applications are said to have good bioavailability in a form suitable for oral administration, and are both designed for dissolution in the stomach.

Janssen adopted a different approach in international patent application PCT/EP97/02507, again for azole antifungals such as itraconazole and saperconazole. In this patent application, the proposed solution to the bioavailability problem is to form a solid dispersion of the practically insoluble drug and a water soluble polymer, with ratios of drug to polymer that aim to dissolve the drug to ensure that the required bioavailability is obtained.

Another approach is reported in the article "Oral Absorption Improvement of Poorly Soluble Drug Using Solid Dispersion Technique" by T. Kai et al (Chem. Pharm. Bull. 44(3) 568–571(1996)) in relation to another antifungal agent, again said to be of low solubility and exhibiting poor oral absorption characteristics. In this article, a solid dispersion of the drug is formed with an enteric polymer and the dissolution characteristics of the solid dispersion are tested in suitable media at pH 1.2 and pH 6.8, with a view to determining the dissolution state of the drug. The article verifies that the drug at pH 6.8 is fully dissolved (supersaturated) and is thus bioavailable, whereas at pH 1.2 the enteric polymers had not dissolved, preventing dissolution of the drug. The article thus promotes as important the supersaturation (complete dissolution) of the drug to ensure adequate bioavailability.

A final attempt to be illustrated is that of European patent application 98305960.1 to Pfizer Products Inc. This application is again aimed at improving the bioavailability of low-solubility drugs such as glycogen phosphorylase inhibitors, 5-lipoxygenase inhibitors, corticotropic releasing hormone inhibitors and antipsychotics.

The Pfizer patent application suggests the use of a solid dispersion of an enteric polymer (namely, hydroxypropylmethylcellulose acetate succinate [HPMCAS]) with the low-solubility drug, again to produce a supersaturated solution in vivo to ensure adequate bioavailability. Indeed, this application specifically aims to produce a supersaturated solution of the drug in order to keep the drug dissolved for as long as possible after administration.

Further in relation to practically insoluble drugs, it has been reported that many such drugs are formulated into dosage forms that should only be administered with food. For example, a commercially available itraconazole dosage form (Sporanox™) is only prescribed for use with food because of relatively poor bioavailability results when administered under fasted conditions.

It is an aim of the present invention to provide a pharmaceutical composition with improved bioavailability for drugs that are considered to be practically insoluble.

However, before turning to discuss the invention, it should be appreciated that the above discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia or elsewhere before the priority date of each claim of this application.

SUMMARY OF THE INVENTION

The present invention provides a pharmaceutical composition of a practically insoluble drug, wherein the composition may be administered with food or without food. In this form of the invention, the composition may be in the form of a solid dispersion of the practically insoluble drug and a polymer having acidic functional groups, and the composition may in vitro form a suspension.

The present invention also provides a pharmaceutical composition of a practically insoluble drug, the composition having an AUC under fed conditions that is 80% to 125% of the composition's AUC under fasted conditions. In this form of the invention, the composition may be in the form of a solid dispersion of the practically insoluble drug and a polymer having acidic functional groups, and the composition may in vitro form a suspension.

Further, the present invention provides a pharmaceutical composition of a practically insoluble drug, wherein in vitro the composition forms a suspension. In a preferred form, the composition may be in the form of a solid dispersion of the practically insoluble drug and a polymer having acidic functional groups.

Of course, in all forms of the present invention, and as will be explained below, it will be appreciated that the pharmaceutical composition may include other components within it, such as disintegrants, diluents, fillers and the like.

Various terms that will be used throughout this specification have meanings that will be well understood by a skilled addressee. However, for ease of reference, some of these terms will now be defined.

The term "practically insoluble" as used herein applies to drugs that are essentially totally water-insoluble or are at least poorly water-soluble. More specifically, the term is applied to any drug that has a dose (mg) to aqueous solubility (mg/ml) ratio greater than 100 ml, where the drug solubility is that of the neutral (for example, free base or free acid) form in unbuffered water. This meaning is to include, but is not to be limited to, drugs that have essentially no aqueous solubility (less than 1.0 mg/ml).

The term "drug" will be widely understood and denotes a compound having beneficial prophylactic and/or therapeutic properties when administered to, for example, humans. Further, the term "drug per se" is used throughout this specification for the purposes of comparison, and means the drug when in an aqueous solution/suspension without the addition of any excipients.

The term "a solid dispersion" in general means a system in solid state comprising at least two components, wherein one component is dispersed more or less evenly throughout the other component or components. In particular, and with reference to a widely accepted definition from the early 1970's, "solid dispersions" are the dispersion of one or more active ingredients in an inert carrier or matrix at solid state, prepared by the melting, solvent, or melting-solvent methods.

The term "in vivo" in general means in the living body of a plant or animal, whereas the term "in vitro" generally means outside the body and in an artificial environment.

Reference throughout this specification will be made to the administration of a pharmaceutical composition under fed conditions or fasted conditions. It is well understood in the art that the pharmacokinetic performance of some compositions is affected by the presence or not of food in the gastro-intestinal system. Other compositions are not so affected. These references thus relate to the normally accepted administration circumstances that are referred to in the art as 'fed' or 'fasted'.

Reference will also be made to the pharmacokinetic parameter AUC. This is a widely accepted parameter determined from the graphical presentation of actual or theoretical plasma profiles (concentration vs time), and represents the area under the curve (AUC) of such a profile.

General Description of the Invention

Returning now to a general description of the present invention, in one form of the invention the pharmaceutical composition is such that, upon administration, a suspension is formed in vivo. Preferably, the suspension is a homogeneous dispersion of particles (containing the drug), the particles at least being of a size where, in vitro, they diffract light such that the suspension presents as a cloudy suspension. Thus, evidence of the presence of such a cloudy suspension can be seen during in vitro dissolution testing of the solid dispersion of the inventive composition.

The particles in the cloudy suspension in vitro will generally be particles of a size greater than about 1 nm but less than about 10 micrometre. In vitro dissolution testing of a pharmaceutical composition according to this form of the present invention reveals that particles in this size range are present when tested at a pH in the range of 5.5 to 7.5. Additionally, when pretreated at acidic pH (namely, when suspended in a dissolution medium at a pH of about 1.2 for a period of about 20 minutes), in vitro dissolution testing of a pharmaceutical composition according to this form of the present invention again reveals that particles in this size range are present when subsequently tested at a pH in the range of 5.5 to 7.5. This pre-treatment may be conducted to simulate in vivo conditions.

In one form of the present invention, it may be preferred for a portion of the particles to be present in nanoparticulate form, such as in the range of 1 nm to 450 nm, and a portion to be present in microparticulate form (such as in the range of 0.45 micrometre to 10 micrometre). The presence of such nanoparticles in vivo may be determined by testing for them in vitro, such as by passing the cloudy suspension through a 450 nm filter and having the suspension remain cloudy. Such nanoparticles are preferably present regardless of whether the acidic pre-treatment step described above is utilised in the testing procedure.

Therefore, the present invention additionally provides a pharmaceutical composition of a practically insoluble drug, wherein the composition forms a suspension in vitro at a pH in the range of 5.5 to 7.5, the suspension having particles in the size range of 1 nm to 10 micrometre, with or without a pre-treatment at acidic pH. Preferably, the suspension has at least a portion of its particles in the size range of 1 nm to 450 nm in vitro at a pH in the range of 5.5 to 7.5, again with or without a pre-treatment at acidic pH.

In this preferred form, the pharmaceutical composition may therefore provide for acceptable absorption of the practically insoluble drug (where acceptable absorption is indicated by the extent of the absorption being greater than that of the crystallised form of the drug per se), in the intestines where the pH is expected to be in the range of 5.5 to 7.5.

In another form of the present invention (as mentioned above), the pharmaceutical composition may be administered with food or without food. This is beneficial as many practically insoluble drugs are unable to be formulated in a manner that allows administration without food, particularly those typically formulated as solid dosage forms. This makes administration of these dosage forms cumbersome and quite inflexible for the patient. Indeed, the pharmaceutical composition of the present invention is preferably bioequivalent when administered under fed conditions compared to administration under fasted conditions. In particular, the AUC for a composition administered under fed conditions is preferably within the range of 80 to 125% of the AUC under fasted conditions, when considering the 90% confidence interval for the ratio of the fed value to the fasted value (using natural log transformed data).

Any practically insoluble drug may be beneficially used in the pharmaceutical composition of the present invention. In this respect, it should be appreciated that while the specification will here list various drugs that are typically considered to be practically insoluble, many drugs (whether considered practically insoluble or not) will have versions (crystalline forms, polymorphs, etc) that are in fact practically insoluble. Also, it is to be appreciated that drugs developed in the future that are also considered to be practically insoluble, are also to be included within the scope of the present invention.

While the specific benefits of the pharmaceutical composition of the present invention have been established by the inventors for azole antifungal drugs, such as itraconazole and saperconazole, similar benefits will be available for other classes of drugs such as anti-hypertensives, immunosuppressants, anti-inflammatories, diuretics, antiepileptics, cholesterol lowering drugs, hormonals hypoglycemics, antiviral drugs, nasal decongestants, antimicrobials, anti-arrthrytics, analgesics, anti-cancer drugs, anti-parasitics, proteins, peptides, CNS stimulants, CNS depressants, 5 HT inhibitors, anti-schizophrenics, anti-Alzheimer drugs, anti-psoriatics, steroidals, oligonucleotides, anti-ulcer drugs, proton pump inhibitors, anti-asthmatics, thrombolyitics and vitamins.

Indeed, even though the following description will mainly describe embodiments of the invention with respect to azole antifungal drugs, it is to be appreciated that the invention is not to be so limited.

The polymers useful for forming the solid dispersion of the pharmaceutical composition of the present invention are those having acidic functional groups. In a preferred form, such polymers will be polycarboxylic acids. Such polycarboxylic acids may be any polycarboxylic acid which, when in a solid dispersion with a practically insoluble drug, results in the formation of the abovementioned suspension, ideally in the preferred pH ranges, and preferably to provide acceptable absorption in the intestines.

Such polymers may be one or more of the group comprising hydroxypropyl methylcellulose phthalate, polyvinyl acetate phthalate (PVAP), hydroxypropylmethylcellulose acetate succinate (HPMCAS), alginate, carbomer, carboxymethyl cellulose, methacrylic acid copolymer, shellac, cellulose acetate phthalate (CAP), starch glycolate, polacrylin, methyl cellulose acetate phthalate, hydroxypropylcellulose acetate phthalate, cellulose acetate terephthalate, cellulose acetate isophthalate and cellulose acetate trimellitate, and includes the various grades of each polymer such as HPMCAS-LF, HPMCAS-MF and HPMCAS-HG.

In a particularly preferred form of the present invention, the polymer is a polycarboxylic acid such as a hydroxypropyl methylcellulose phthalate such as that available from Shin-Etsu Chemical Industry Co Ltd as HP-50, HP-55 or HP-55S. However, it is envisaged that alternatives such as the use of an aqueous based enteric polymer, such as the dispersion Eudragit L30D, or enteric polymers dissolved in water with the addition of ammonia or alkaline agents, may be useful.

In relation to amounts of drug and the polymer in the solid dispersion, the ratio of drug to polymer may be in the range of from 3:1 to 1:20. However, ratios in the narrower range of 3:1 to 1:5 are preferred. An even more preferred range is 1:1 to 1:3, with the most preferred ratio being about 1:1.5 (or 2:3).

The solid dispersion of the composition of the present invention is preferably formed by spray. drying techniques, although it will be understood that suitable solid dispersions may be formed by a skilled addressee utilising other conventional techniques, such as co-grinding, melt extrusion, freeze drying, rotary evaporation or any solvent removal process.

In the preferred spray drying technique, the solid dispersion is formed by dispersing or dissolving the drug and the polymer in a suitable solvent, and subsequently spray drying to form the solid dispersion in the form of a powder. Suitable solvents or dispersion media include methylene chloride, chloroform, ethanol, methanol, propan-2-ol, ethylacetate, acetone, water or mixtures thereof.

Other excipients may then be blended into the powder (with or without milling or grinding) to form a composition suitable for use in dosage forms such as tablets and capsules.

The present invention therefore also provides a process for preparing a pharmaceutical composition of a practically insoluble drug, the process including dispersing in a solvent the drug and a polymer having acidic functional groups, and spray drying the dispersion to form a solid dispersion.

The present invention may thus provide a process for preparing a pharmaceutical composition of a practically insoluble drug, where the process includes the steps of:
 (a) adding a polymer having acidic functional groups to a solvent to form a dispersion;
 (b) adding the drug to the dispersion to form a suspension or solution; and
 (c) spray drying the suspension or solution to form the pharmaceutical composition in the form of a solid dispersion.

Alternatively, the present invention may provide a process for preparing a pharmaceutical composition of a practically insoluble drug, where the process includes the steps of:
 (a) adding the drug to a solvent to form a dispersion;
 (b) adding a polymer having acidic functional groups drug to the dispersion to form a suspension or solution; and
 (c) spray drying the suspension or solution to form the pharmaceutical composition in the form of a solid dispersion.

The composition of the present invention may be formulated into pharmaceutical dosage forms comprising a therapeutically effective amount of the composition. Although pharmaceutical dosage forms for oral administration, such as tablets and capsules, are envisaged, the composition of the present invention can also be used to prepare other pharmaceutical dosage forms, such as for rectal, vaginal, ocular or buccal administration, or the like. It should also be appreciated that the solid dispersions of the composition of the invention may be spray coated (or the like) onto cores to produce particles suitable for use in any of these dosage forms.

It will also be appreciated that various of these dosage forms may include a range of traditional excipients such as disintegrants, diluents, fillers, lubricants, glidants, colourants and flavours.

For example, suitable disintegrants may be those that have a large coefficient of expansion, and examples may include crosslinked polymers such as crospovidone (crosslinked polyvinylpyrrolidone), croscarmellose (crosslinked sodium carboxymethylcellulose), and sodium starch glycolate.

Also, it will be appreciated that it may be advantageous to add to a dosage form an inert substance such as a diluent or a filler. A variety of materials may be used as diluents or fillers, and examples may be sucrose, dextrose, mannitol, sorbitol, starch, micro-crystalline cellulose, and others known in the art, and mixtures thereof.

Lubricants and glidants may be employed in the manufacture of certain dosage forms, and will usually be employed when producing tablets. Examples of lubricants and glidants are hydrogenated vegetable oils, magnesium stearate, stearic acid, sodium lauryl sulfate, magnesium lauryl sulfate, colloidal silica, talc, mixtures thereof, and others known in the art. A preferred lubricant is magnesium stearate, or mixtures of magnesium stearate with colloidal silica. Excipients such as colouring agents and pigments may also be added to dosage forms in accordance with the present invention, and suitable colouring agents and pigments may include titanium dioxide and dyes suitable for food.

Flavours may be chosen from synthetic flavour oils and flavouring aromatics or natural oils, extracts from plants, leaves, flowers, fruits and so forth and combinations thereof. These may include cinnamon oil, oil of wintergreen, peppermint oils, bay oil, anise oil, eucalyptus, thyme oil. Also useful as flavours are vanilla, citrus oil, including lemon, orange, grape, lime and grapefruit, and fruit essences including apple, banana, pear, peach, strawberry, raspberry, cherry, plum, pineapple, apricot and so forth.

With reference to the pharmocokinetic performance of pharmaceutical compositions in accordance with the present invention, it will be appreciated that the parameters that are commonly used in the art to describe the in vivo performance of a formulation (or the bioavailability) are $C_{max}$ (the maximum concentration of the active in the blood) and, as mentioned previously, AUC (area under the curve—a measure of the total amount of drug absorbed by the patient). These are also the parameters used by regulatory agencies around the world to assess bioequivalence of different formulations. For instance, to be considered bioequivalent, the 90% confidence interval for the ratio of the test to reference product (using natural log-transformed data) for $C_{max}$ and AUC are within the range of 80 to 125%.

By utilising compositions in accordance with the present invention, it has been found that drugs previously considered to present bioavailability problems may be presented in dosage forms with superior bioavailability. For instance, and as will be described in more detail below with respect to two examples, where the drug is itraconazole the inventive compositions have produced formulations that are not considered bioequivalents to, but have at least twice the bioavailability of, a commercially available itraconazole product (Sporanox™). Additionally, and again in comparison with Sporanox™, the inventive compositions have produced formulations that have reduced food effect and thus need not be administered with food (unlike Sporanox™).

Furthermore, the present invention also provides a pharmaceutical composition in the form of a solid dispersion of a polymer with acidic functional groups (preferably a polycarboxylic acid such as a hydroxypropyl methylcellulose phthalate) and an azole antifungal drug (such as itraconazole), wherein in vitro the composition forms a suspension. Preferably, the composition upon administration forms a suspension at a pH in the range of 4.0 to 8.0, but more preferably in the range 5.5 to 7.5, and may provide acceptable absorption in the intestines.

The present invention further provides a pharmaceutical composition in the form of a solid dispersion of a hydroxypropyl methylcellulose phthalate and a practically insoluble drug, wherein the composition forms a suspension in vitro in the pH range of 4.0 to 8.0 (preferably 5.5 to 7.5) and preferably provides acceptable absorption in the intestines.

Finally, in a preferred form the present invention is a pharmaceutical composition in the form of a solid dispersion of itraconazole that provides a mean $C_{max}$ of at least 100 ng/ml when a dose of 100 mg of itraconazole is given in the fasted state. A more preferred form is such a formulation of itraconazole that provides a mean $C_{max}$ of 150 to 250 ng/ml, when a dose of 100 mg of itraconazole is given in the fasted state.

A further form of the present invention is a pharmaceutical composition in the form of a solid dispersion of itraconazole that provides a mean AUC at least 800 ng.h/ml when a dosage of 100 mg of itraconazole is given in the fasted state. A more preferred form is such a solid dispersion of itraconazole that provides a mean AUC of 1300 to 2300 ng.h/ml, when a dose of 100 mg of itraconazole is given in the fasted state.

For formulations in accordance with the present invention containing drugs other than itraconazole it is preferred that the bioavailability of the drug as compared to the drug per se is improved by at least 50% and more preferably 100%, in terms of AUC.

DESCRIPTION OF THE PREFERRED EMBODIMENTS

Reference will now be made to examples that embody the above general principles of the present invention. However, it is to be understood that the following description is not to limit the generality of the above description.

EXAMPLE 1

To produce the solid dispersion, a solution was prepared by dispersing HP-50 (60 g) in methylene chloride (1200 g) and then adding itraconazole (40 g) and stirring to form a pale brown solution. This solution was then spray dried to form a powder.

A portion (38.96 g) of this spray dried powder was then blended with sodium starch glycolate (14.87 g) and colloidal silicon dioxide (Aerosil 200) (0.75 g) in a mortar and pestle for 5 minutes. Magnesium stearate (1.11 g) was added to the blend from the mortar and the mixture tumble blended until uniform.

This powder blend was then filled into size 0 gelatin capsules by hand. Each capsule was filled with 364 to 378 mg of powder, containing nominally 98 to 102 mg of itraconazole.

These capsules were tested in a standard USP type 11 dissolution bath (paddle method). A capsule was weighted with stainless steel wire and then dropped into 900 ml of dissolution media consisting of 0.05 M phosphate buffer solution adjusted to pH 6.0. Samples of this media were extracted at appropriate time intervals through a 10 micrometre filter and the content of itraconazole in the sample assayed using a HPLC method. Both the media in the dissolution bath and the extracted, filtered samples were cloudy in appearance. This test was also performed using 900 ml of hydrochloric acid acidic media (pH 1.2, 0.06 M HCl). In this case both the media and the samples were clear.

The measured amount of itraconazole present in the samples, as a percentage of the total possible amount, after various times in the test described above is presented in the table below. For comparison the results of the same tests performed on a marketed itraconazole capsule (Sporanox™) are also tabulated. Sporanox™ produced clear solutions in both media.

| Time (min) | Sporanox ™ 98P0800E | Test Example 1 |
|---|---|---|
| pH 1.2 media, 75 rpm, paddles | | |
| 0 | | 0 |
| 5 | 1.9 | 4 |
| 10 | 5.2 | 6.4 |
| 30 | 42.3 | 9.9 |
| 45 | 56.1 | 11.6 |
| 60 | 64 | 13 |
| 120 | 76.2 | 16.6 |
| 180 | | 18.8 |
| 240 | | 21.1 |

-continued

| Time (min) | Sporanox ™ 98P0800E | Test Example 1 |
|---|---|---|
| pH 6.0 media, 100 rpm, paddles | | |
| 0 | 0 | 0 |
| 5 | 1.1 | 4 |
| 10 | 1.2 | 20.2 |
| 30 | 2.2 | 58.5 |
| 45 | 2.8 | 69.7 |
| 60 | 3.2 | 76.4 |
| 120 | 3.7 | 77.6 |
| 180 | | 82.3 |
| 240 | | 81.1 |

EXAMPLE 2

To produce the solid dispersion, a solution was prepared by dispersing HP-50 (420 g) in methylene chloride (8400 g) and then adding itraconazole (280 g) and stirring to form a pale brown solution. This solution was then spray dried to form a powder.

A portion (292 g) of this spray dried powder was then blended with sodium starch glycolate (93.6 g) and colloidal silicon dioxide (Aerosil 200) (5.6 g) in a Collette mixer at high speed for 5 minutes. Magnesium stearate (8.8 g) was added to the blend from the Collette mixer and the mixture tumble blended until uniform.

This powder blend was then filled into size 0 gelatin capsules by hand. Each capsule was filled with 345 to 359 mg of powder, containing nominally 98 to 102 mg of itraconazole.

These test capsules were utilised in a pharmacokinetic study. 8 male volunteers were dosed with one 100 mg capsule after an overnight (10 hour) fast. The capsules were dosed with 240 ml water. At appropriate time intervals blood samples were taken from the subjects and the concentration of itraconazole in the plasma determined. The study was performed in a randomised 2 way crossover fashion with subjects receiving 100 mg itraconazole as a marketed capsule (Sporanox™) or as the test formulation described in example 2 above. The alternate dose was taken after a 2 week washout period.

A plot of the mean blood levels measured is as follows:

The data was analysed and the following standard mean pharmacokinetic parameters were obtained.

| Parameter | Example capsule | Sporanox ™ capsule (Lot 98P0800E) | Ratio |
|---|---|---|---|
| $C_{max}$ (ng/ml) | 182.6 | 56.0 | 326% |
| $T_{max}$ (h) | 2.94 | 3.44 | 85.5% |
| AUC (ng.h/ml) | 1776 | 622 | 285% |
| $AUC_{inf}$ (ng.h/ml) | 1875 | 664 | 282% |

It can be seen from these results that significantly higher plasma itraconazole levels are obtained from the formulation described in the example than the marketed capsule form under these conditions.

Indeed, it was expected that the itraconazole formulation of this invention would have a later $T_{max}$ (time to maximum blood concentration of active) than Sporanox™, due to the use of an enteric polymer, which should not have solubilised until after passing through the stomach. This is in comparison to the water-soluble polymers used in Sporanox™ that would solublise in the stomach.

However, it can be seen from the above data that the $T_{max}$ of the formulation of the present invention is at least similar to the $T_{max}$ of Sporanox™, if not shorter than it. Together with the greatly increased $C_{max}$, this result was surprising.

EXAMPLE 3

Test capsules from Example 2 containing 100 mg of itraconazole were also utilised in a pharmacokinetic study under fed conditions, primarily for comparison with the pharmacokinetic results of Example 2 to determine whether there was any food effect.

The study was again conducted as a single dose, crossover study in 8 health male adult subjects, but under fed conditions. The subjects commenced eating a standard high fat breakfast 20 minutes prior to dose administration, having fasted for at least 10 hours prior to that.

A two week washout period between administration of the dose for each of the two treatments was again used, and the comparative product was again two 100 mg itraconazole capsules marketed as Sporanox™.

At appropriate time intervals blood samples were taken from the subjects and the concentration of itraconazole in the plasma determined.

Figure 2:
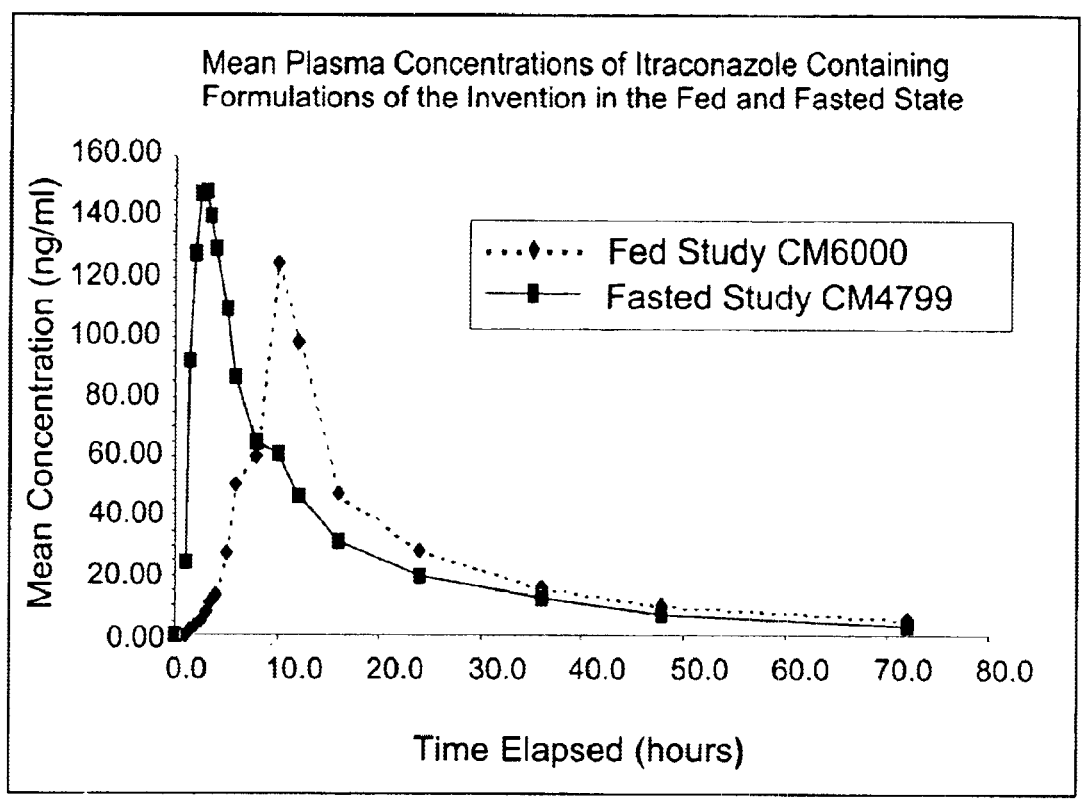

A plot of the mean blood levels from the fasted study of example 2 (Fasted Study CM4799) and the fed study of Example 3 (Fed Study CM6000) is as shown in FIG. 2.

The data from the fed study of Example 3 was analysed and the following mean standard pharmacokinetic parameters were obtained:

| Parameter | Example 3 Capsule (Fed) | Example 2 Capsule (Fasted) |
|---|---|---|
| $C_{max}$ (ng/ml) | 148.20 | 182.6 |
| $T_{max}$ (h) | 10.25 | 2.94 |
| AUC (ng.h/ml) | 1806 | 1776 |
| $AUC_{inf}$ (ng.h/ml) | 1997 | 1875 |

It can be seen from these results that the example formulation produces plasma profiles considered bioequivalent in terms of AUC under fasting and fed conditions, due to the AUC under fed conditions being about 102% of the AUC under fasted conditions, which is well within the range of 80 to 120%. This is an indication that the total amount of drug absorbed over time is essentially equivalent under fed and fasted conditions.

Finally, it will be appreciated that there may be other variations and modifications to the compositions described herein that are also within the scope of the present invention.

What is claimed is:

1. A pharmaceutical composition consisting essentially of about 100 mg of an azole antifungal drug and optionally at least one polymer having acidic functional groups wherein in vivo the composition provides a mean $C_{MAX}$ of at least 100 ng/ml, after administration in the fasted state.

2. A pharmaceutical composition according to claim 1, wherein said at least one polymer having acidic functional groups is present.

3. A pharmaceutical composition according to claim 1, wherein in vivo the composition provides a mean $C_{MAX}$ of at least 150 to 250 ng/ml, after administration of the azole antifungal drug in the fasted state.

4. A pharmaceutical composition according to claim 1, wherein the azole antifungal drug is itraconazole.

5. A pharmaceutical composition consisting essentially of about 100 mg of an azole antifungal drug and optionally at least one polymer having acidic functional groups wherein the composition provides a mean AUC of at least 800 ng.h/ml, after administration in the fasted state.

6. A pharmaceutical composition according to claim 5, wherein said at least one polymer having acidic functional groups is present.

7. A pharmaceutical composition according to claim 5, wherein the composition provides a mean AUC of 1300 to 2300 ng.h/ml, after administration of the azole antifungal drug in the fasted state.

8. A pharmaceutical composition according to claim 5, wherein the azole antifungal drug is itraconazole.

9. A pharmaceutical composition, consisting essentially of:

about 100 mg of an azole antifungal drug; and one or more polymer having acidic functional groups; and optionally one or more additional ingredients selected from the group consisting of a disintegrant, a diluent, a filler, an inert solid carrier, an inert solid matrix, a lubricant, a glidant, a colouring agent, a pigment, a flavour, water, ammonia, an alkaline agent, and methylene chloride, wherein in vivo the composition provides a mean $C_{MAX}$ of at least 100 ng/ml, after administration in the fasted state.

10. A pharmaceutical composition according to claim 9, which is present in a capsule.

11. A pharmaceutical composition according to claim 9, in the form of a powder.

12. A pharmaceutical composition, consisting essentially of:

about 100 mg of an azole antifungal drug; and one or more polymer having acidic functional groups; and optionally one or more additional ingredients selected from the group consisting of a disintegrant, a diluent, a filler, an inert solid carrier, an inert solid matrix, a lubricant, a glidant, a colouring agent, a pigment, a flavour, water, ammonia, an alkaline agent, and methylene chloride, wherein in vivo the composition provides a mean AUC of at least 800 ng.h/ml, after administration in the fasted state.

13. A pharmaceutical composition according to claim 12, which is present in a capsule.

14. A pharmaceutical composition according to claim 12, in the form of a powder.

15. A pharmaceutical composition, consisting essentially of:

about 100 mg of an itraconazole; and one or more polymer selected from the group consisting of hydroxypropylmethylcellulose phthalate, polyvinyl acetate phthalate, hydroxypropylmethylcellulose acetate succinate, alginate, carbomer, carboxymethyl cellulose, methacrylic acid copolymer, shellac, cellulose acetate phthalate, starch glycolate, polacrylin, methyl cellulose acetate phthalate, hydroxypropylcellulose acetate phthalate, cellulose acetate terephthalate, cellulose acetate isophthalate and cellulose trimellitate; and optionally one or more additional ingredients selected from the group consisting of a disintegrant, a diluent, a filler, an inert solid carrier, an inert solid matrix, a lubricant, a glidant, a colouring agent, a pigment, a flavour, water, ammonia, an alkaline agent, and methylene chloride, wherein in vivo the composition provides a mean $C_{MAX}$ of at least 100 ng/ml, after administration in the fasted state.

16. A pharmaceutical composition, consisting essentially of:

about 100 mg of an itraconazole; and one or more polymer selected from the group consisting of hydroxypropylmethylcellulose phthalate, polyvinyl acetate phthalate, hydroxypropylmethylcellulose acetate succinate, alginate, carbomer, carboxymethyl cellulose, methacrylic acid copolymer, shellac, cellulose acetate phthalate, starch glycolate, polacrylin, methyl cellulose acetate phthalate, hydroxypropylcellulose acetate phthalate, cellulose acetate terephthalate, cellulose acetate isophthalate and cellulose trimellitate; and optionally one or more additional ingredients selected from the group consisting of a disintegrant, a diluent, a filler, an inert solid carrier, an inert solid matrix, a lubricant a glidant, a colouring agent, a pigment, a flavour, water, ammonia, an alkaline agent, and methylene chloride, wherein in vivo the composition provides a mean AUC of at least 800 ng.h/ml, after administration in the fasted state.

* * * * *